(12) United States Patent
Wiederin et al.

(10) Patent No.: US 9,733,158 B1
(45) Date of Patent: Aug. 15, 2017

(54) DILUTION INTO A TRANSFER LINE BETWEEN VALVES FOR MASS SPECTROMETRY

(71) Applicant: Elemental Scientific, Inc., Omaha, NE (US)

(72) Inventors: Daniel R. Wiederin, Omaha, NE (US); Austin Schultz, Omaha, NE (US)

(73) Assignee: Elemental Scientific, Inc., Omaha, NE (US)

( * ) Notice: Subject to any disclaimer, the term of this patent is extended or adjusted under 35 U.S.C. 154(b) by 58 days.

(21) Appl. No.: 14/830,052

(22) Filed: Aug. 19, 2015

Related U.S. Application Data

(60) Provisional application No. 62/039,317, filed on Aug. 19, 2014.

(51) Int. Cl.
*G01N 1/14* (2006.01)

(52) U.S. Cl.
CPC ..................... *G01N 1/14* (2013.01)

(58) Field of Classification Search
CPC ........................................................ G01N 1/14
USPC ....................................................... 73/864.34
See application file for complete search history.

(56) References Cited

U.S. PATENT DOCUMENTS

| | | | | |
|---|---|---|---|---|
| 3,039,309 A * | 6/1962 | Vesper | ................. | F04B 43/1133 417/394 |
| 4,828,660 A * | 5/1989 | Clark | ....................... | B01D 1/02 134/109 |
| 6,083,754 A * | 7/2000 | Sakurai | ................... | G01N 21/25 422/81 |
| 6,171,552 B1 * | 1/2001 | Takeya | ..................... | G01N 1/34 422/68.1 |
| 6,309,550 B1 * | 10/2001 | Iversen | .................. | B01D 53/22 210/640 |
| 8,118,050 B1 * | 2/2012 | Wiederin | ................. | G01N 1/38 137/111 |
| 8,371,181 B2 * | 2/2013 | Wiederin | ................ | F04B 13/00 417/62 |
| 8,453,524 B2 * | 6/2013 | Kawabata | ................ | G01N 1/38 137/565.11 |
| 2003/0109061 A1 * | 6/2003 | Eaton | ....................... | G01N 1/38 436/180 |
| 2004/0002166 A1 * | 1/2004 | Wiederin | ............. | G01N 1/2202 436/181 |
| 2006/0073608 A1 * | 4/2006 | Saini | ...................... | B01J 41/046 436/174 |

(Continued)

*Primary Examiner* — Lisa Caputo
*Assistant Examiner* — Philip Cotey
(74) *Attorney, Agent, or Firm* — Advent, LLP

(57) ABSTRACT

A system can include a sampler assembly configured to collect a viscous sample at a first location. In implementations, the viscous sample includes concentrated sulfuric acid (e.g., greater than about 75% $H_2SO_4$). The system can also include a valve coupled with the sampler assembly for receiving the viscous sample. The valve is configured to couple with a source of a diluent and a sample transfer line. The system further includes a pump coupled with the valve for injecting the diluent into the sample transfer line along with the viscous sample to dilute the viscous sample and transport the diluted sample to a second location remote from the first location via the sample transfer line. In implementations, the sample transfer line is at least approximately two meters in length.

20 Claims, 1 Drawing Sheet

(56) References Cited

U.S. PATENT DOCUMENTS

| | | | | |
|---|---|---|---|---|
| 2006/0104827 A1* | 5/2006 | Shaw | ........................ | G01N 1/38 417/245 |
| 2006/0127237 A1* | 6/2006 | Shaw | ........................ | G01N 1/38 417/313 |
| 2007/0141720 A1* | 6/2007 | Stewart | .................. | B01J 41/046 436/178 |
| 2009/0046282 A1* | 2/2009 | Hong | ...................... | G01N 21/05 356/246 |
| 2013/0321803 A1* | 12/2013 | Kohara | .................. | G01N 21/69 356/313 |

* cited by examiner

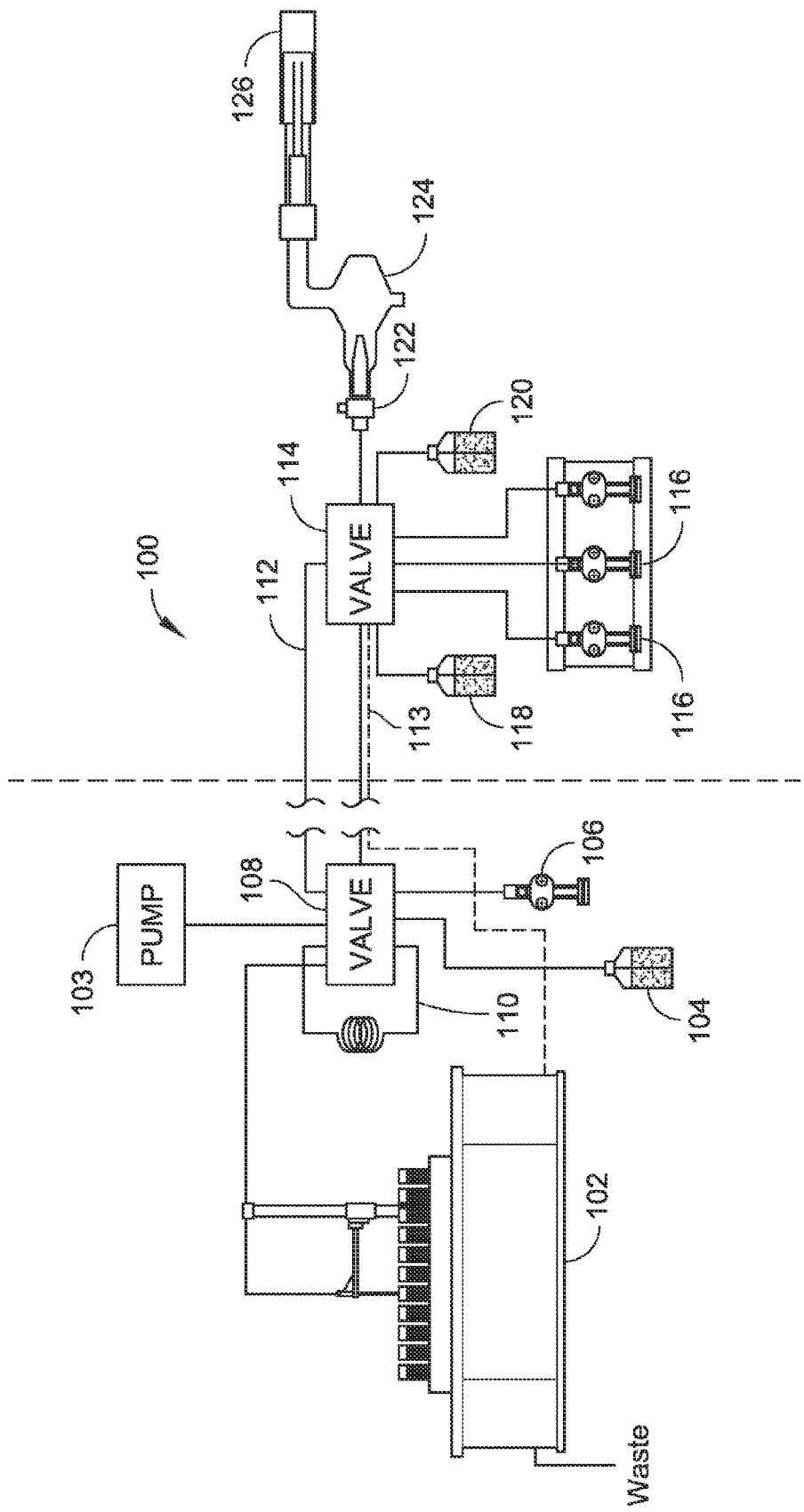

DILUTION INTO A TRANSFER LINE BETWEEN VALVES FOR MASS SPECTROMETRY

CROSS-REFERENCE TO RELATED APPLICATIONS

The present application claims the benefit under 35 U.S.C. §119(e) of U.S. Provisional Application Ser. No. 62/039,317, filed Aug. 19, 2014, and titled "DILUTION INTO A TRANSFER LINE BETWEEN VALVES FOR MASS SPECTROSCOPY." U.S. Provisional Application Ser. No. 62/039,317 is herein incorporated by reference in its entirety.

BACKGROUND

Inductively Coupled Plasma (ICP) spectrometry is an analysis technique commonly used for the determination of trace element concentrations and isotope ratios in liquid samples. ICP spectrometry employs electromagnetically generated partially ionized argon plasma which reaches a temperature of approximately 7,000K. When a sample is introduced to the plasma, the high temperature causes sample atoms to become ionized or emit light. Since each chemical element produces a characteristic mass or emission spectrum, measuring the spectra of the emitted mass or light allows the determination of the elemental composition of the original sample.

Sample introduction systems may be employed to introduce the liquid samples into the ICP spectrometry instrumentation (e.g., an Inductively Coupled Plasma Mass Spectrometer (ICP/ICP-MS), an Inductively Coupled Plasma Atomic Emission Spectrometer (ICP-AES), or the like) for analysis. For example, a sample introduction system may withdraw an aliquot of a liquid sample from a container and thereafter transport the aliquot to a nebulizer that converts the aliquot into a polydisperse aerosol suitable for ionization in plasma by the ICP spectrometry instrumentation. The aerosol is then sorted in a spray chamber to remove the larger aerosol particles. Upon leaving the spray chamber, the aerosol is introduced into the plasma by a plasma torch assembly of the ICP-MS or ICP-AES instruments for analysis.

SUMMARY

A system can include a sampler assembly configured to collect a viscous sample at a first location. In implementations, the viscous sample includes concentrated sulfuric acid (e.g., greater than about 75% $H_2SO_4$). The system can also include a valve coupled with the sampler assembly for receiving the viscous sample. The valve is configured to couple with a source of a diluent and a sample transfer line. The system further includes a pump coupled with the valve for injecting the diluent into the sample transfer line along with the viscous sample to dilute the viscous sample and transport the diluted sample to a second location remote from the first location via the sample transfer line. In implementations, the sample transfer line is at least approximately two meters in length.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures.

FIG. 1 is a diagrammatic illustration of a system for providing dilution into a transfer line between valves (e.g., of mass spectrometry equipment) in accordance with an example embodiment of the present disclosure.

DETAILED DESCRIPTION

ICP spectrometry can be utilized to determine the composition of a sample material (e.g., a sample solution with an unknown composition, a standard solution, etc.) with high degrees of accuracy. In various ICP spectrometry environments, the sample to be analyzed can include a highly viscous sample, which can pose problems related to the handling and transportation of the highly viscous sample in order to analyze the sample with ICP spectrometry instrumentation. For instance, the highly viscous sample can have flow restrictions within the tubing utilized to maneuver and/or process the highly viscous sample, particularly where the system tubing includes relatively small internal diameters. Attempting pressure-driven processes for transporting the highly viscous sample can risk contamination of the highly viscous sample, which is typically present in a relatively high purity state. Similarly, attempting to manually dilute a highly viscous material prior to analysis of the sample can risk contamination of the sample, due at least in part to the rigorous demands in maintaining a sterile manual dilution atmosphere.

Accordingly, the present disclosure is directed to a method of manipulating highly viscous samples that utilizes automatic and direct sampling and dilution of the highly viscous sample to provide a diluted sample for analysis. In implementations, the highly viscous sample is loaded at a first location into a sample loop under controlled conditions (e.g., via a syringe pump or vacuum pump), where the sample loop is positioned relatively close to the source of the highly viscous sample (e.g., within approximately 0.8 meters). The highly viscous sample is introduced to a diluent in one or more transfer lines to convey the diluted sample to a valve positioned at a second location remote from the first location. In implementations, the one or more transfer lines are at least approximately two meters in length.

Referring generally to FIG. 1, example systems 100 configured to provide dilution into a transfer line between valves of equipment are described. A system 100 includes a sampler assembly, such as an autosampler 102, for automatically collecting a sample (e.g., a sample for analysis, an internal standard, etc.) from a number of samples contained in test tubes, and so forth at a first location. The autosampler 102 can collect viscous samples for analysis, such as sulfuric acid ($H_2SO_4$), photoresist materials, and the like. In implementations, the autosampler 102 is configured to collect concentrated sulfuric acid for analysis. As used herein, concentrated sulfuric acid refers to sulfuric acid having concentrations of at least about 75% $H_2SO_4$, and can include, for example, sulfuric acid having concentrations of about 98% $H_2SO_4$. Sulfuric acid at 75% $H_2SO_4$, has a viscosity of about 14 centipoise at 70° F., whereas sulfuric acid at 98% $H_2SO_4$ has a viscosity of about 24.5 centipoise at 70° F.

In an implementation a pump 103 is operably coupled to the autosampler 102 to draw the viscous sample (e.g., concentrated sulfuric acid) into the system 100 at the first location. The pump 103 can include, but is not limited to, a syringe pump, a vacuum pump, and the like. A valve 108 (e.g., a rotary valve) is coupled with the autosampler 102 for receiving the viscous sample through action of the pump 103. In implementations, the valve 108 is positioned within one meter (e.g., within approximately 0.8 meters) of the source of the viscous sample, such that the distance traveled by the viscous sample through the fluid lines connecting the autosampler 102 and the valve 108 is manageable by the pump 103. The fluid lines can have, for example, an internal diameter of about 0.8 millimeters (0.8 mm ID), where travel of two meters or more by the viscous sample would be severely restricted due in part to the viscosity of the viscous sample and the dimensions of the fluid lines. The valve 108 is also coupled with a source of a diluent 104. In embodiments of the disclosure, the system 100 includes a pump 106 (e.g., a syringe pump) coupled with the valve 108 for injecting the diluent 104 into one or more sample transfer lines 112 along with the viscous sample to dilute the viscous sample and transport the diluted sample to a second location remote from the first location via the sample transfer line 112. For example, the second location can be separated from the first location by a distance of two meters (2 m), more than two meters (2 m), and so forth, such that an undiluted viscous sample would not feasibly transfer within transfer lines 112 having an internal diameter of about 0.8 millimeters (0.8 mm ID).

In some embodiments, the valve 108 can also be coupled with a sample loop 110 for holding priming fluid and so forth. The system 100 can also include a nebulizer 122 coupled with a cyclonic spray chamber 124 for supplying an Inductively Coupled Plasma (ICP) torch 126 with sample gas, samples from the autosampler 102, internal standard 120, carrier 118, diluent, and so forth. For example, a valve 114 (e.g., a rotary valve) can be coupled with the valve 108 via the one or more transfer lines 112. In implementations, the at least one sample transfer line 112 is coupled to a power line 113 configured to supply power from the autosampler 102 to the valve 114, such that at least a portion of the power line 113 is coupled to the sample transfer line 112. The power line 113 can facilitate the distance of at least two meters between the first location and the second location by supplying power to the valve 114 for operation of the valve 114 without requiring a local power source at the second location to power the valve 114.

The valve 114 can also be coupled with one or more syringe pumps 116, the nebulizer 122, and so forth. The valve 114 can receive samples from the autosampler 102 via the one or more transfer lines 112. For example, the valve 114 can receive the diluted sample, which can include concentrated sulfuric acid that is diluted in the transfer lines 112 via the diluent 104 suppled to valve 108 via the pump 106. The valve 114 can also receive the internal standard 120 (e.g., a continuous or semi-continuous flow of the internal standard 120, a spike of the internal standard 120, etc.), the carrier 118, and/or the diluent and supply them to the nebulizer 122. A peristaltic pump can be used to evacuate waste from the nebulizer 122. For example, the peristaltic pump can be connected to a drain chamber of the nebulizer 122.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A system comprising:
   a sampler assembly configured to collect a sample of concentrated sulfuric acid at a first location;
   a valve coupled with the sampler assembly for receiving the sample of concentrated sulfuric acid, the valve further coupled with a source of a diluent and with a sample transfer line, the sample transfer line having an internal diameter of about 0.8 millimeters;
   a pump coupled with the valve for injecting the diluent into the sample transfer line along with the sample of concentrated sulfuric acid to dilute the sample to furnish a fully liquid diluted sample and transport the fully liquid diluted sample to a second location remote from the first location via the sample transfer line having a length of at least two meters.

2. The system as recited in claim 1, wherein the sample of concentrated sulfuric acid includes sulfuric acid having a concentration of greater than about 75% sulfuric acid.

3. The system as recited in claim 1, wherein the sample of concentrated sulfuric acid includes sulfuric acid having a concentration of about 98% sulfuric acid.

4. The system as recited in claim 1, wherein the valve is located within about one meter from a source of the concentrated sulfuric acid from which the sampler assembly collects the sample of the concentrated sulfuric acid at the first location.

5. The system as recited in claim 1, further comprising:
   a valve at the second location coupled to the sample transfer line, the valve at the second location configured to receive the fully liquid diluted sample via the sample transfer line.

6. The system as recited in claim 5, further comprising:
   a power line configured to supply power between the sampling assembly and the valve at the second location.

7. The system as recited in claim 6, wherein at least a portion of the power line is coupled to the sample transfer line.

8. The system as recited in claim 1, wherein the system is configured to receive an internal standard added using a syringe.

9. The system as recited in claim 1, wherein the system is configured to receive a standard spike added using a syringe.

10. A method comprising:
    collecting a sample of concentrated sulfuric acid at a first location with a sampler assembly;
    receiving a diluent and the sample of concentrated sulfuric acid with a valve assembly;
    injecting the diluent and the sample of concentrated sulfuric acid into a sample transfer line to dilute the sample of concentrated sulfuric acid to furnish a fully liquid diluted sample, the sample transfer line having an internal diameter of about 0.8 millimeters; and
    transferring the fully liquid diluted sample from the first location to a second location via the sample transfer line having a length of at least two meters.

11. The method as recited in claim 10, wherein the sample of concentrated sulfuric acid includes sulfuric acid having a concentration of greater than about 75% sulfuric acid.

12. The method as recited in claim 10, wherein the sample of concentrated sulfuric acid includes sulfuric acid having a concentration of about 98% sulfuric acid.

13. The method as recited in claim 10, wherein the valve assembly is located within about one meter from a source of the concentrated sulfuric acid at the first location.

14. The method as recited in claim 10, further comprising:
  receiving the fully liquid diluted sample with a valve at the second location via the sample transfer line.

15. The method as recited in claim 14, further comprising:
  supplying power between the sampling assembly and the valve at the second location via a power line.

16. The method as recited in claim 15, wherein at least a portion of the power line is coupled to the sample transfer line.

17. A system comprising:
  a sampler assembly configured to collect a sample of concentrated sulfuric acid at a first location, the concentrated sulfuric acid having a concentration of greater than about 75% sulfuric acid;
  a valve coupled with the sampler assembly for receiving the sample of concentrated sulfuric acid, the valve further coupled with a source of a diluent and with a sample transfer line, the sample transfer line having an internal diameter of about 0.8 millimeters, the valve positioned within about one meter from a source of the concentrated sulfuric acid from which the sampler assembly collects the sample of the concentrated sulfuric acid at the first location;
  a pump coupled with the valve for injecting the diluent into the sample transfer line along with the sample of concentrated sulfuric acid to dilute the sample to furnish a fully liquid diluted sample and transport the fully liquid diluted sample to a second location remote from the first location via the sample transfer line having a length of at least two meters.

18. The system as recited in claim 17, wherein the sample of concentrated sulfuric acid includes sulfuric acid having a concentration of about 98% sulfuric acid.

19. The system as recited in claim 17, further comprising:
  a valve at the second location coupled to the sample transfer line, the valve at the second location configured to receive the fully liquid diluted sample via the sample transfer line.

20. The system as recited in claim 19, further comprising:
  a power line configured to supply power between the sampling assembly and the valve at the second location, wherein at least a portion of the power line is coupled to the sample transfer line.

* * * * *